United States Patent
Fleury et al.

(10) Patent No.: US 10,285,725 B2
(45) Date of Patent: May 14, 2019

(54) SNARE DESIGN FOR IMPROVED TRACTION

(71) Applicant: Boston Scientific Scimed, Inc., Maple Grove, MN (US)

(72) Inventors: Sean P. Fleury, Brighton, MA (US); Kenneth R. Keene, Winchester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 526 days.

(21) Appl. No.: 15/050,036

(22) Filed: Feb. 22, 2016

(65) Prior Publication Data

US 2016/0242804 A1  Aug. 25, 2016

Related U.S. Application Data

(60) Provisional application No. 62/120,155, filed on Feb. 24, 2015.

(51) Int. Cl.
| | | |
|---|---|---|
| *A61B 17/12* | (2006.01) | |
| *A61B 17/3205* | (2006.01) | |
| *A61B 17/00* | (2006.01) | |
| *A61B 18/14* | (2006.01) | |

(52) U.S. Cl.
CPC .. *A61B 17/32056* (2013.01); *A61B 17/00234* (2013.01); *A61B 17/12013* (2013.01); *A61B 2017/00269* (2013.01); *A61B 2018/141* (2013.01)

(58) Field of Classification Search
CPC ...... A61B 17/32056; A61B 2018/1407; A61B 2018/141; A61B 2017/2212; A61B 17/221; A61B 2017/32006; A61B 17/26
See application file for complete search history.

(56) References Cited

U.S. PATENT DOCUMENTS

| | | |
|---|---|---|
| 5,078,716 A | 1/1992 | Doll |
| 5,893,859 A | 4/1999 | Marin et al. |
| 2003/0139750 A1 | 7/2003 | Shinozuka et al. |
| 2004/0220604 A1* | 11/2004 | Fogarty .............. A61B 17/0218 606/190 |
| 2012/0172864 A1 | 7/2012 | Farin et al. |
| 2013/0018384 A1* | 1/2013 | Kappel ............ A61B 17/32056 606/111 |
| 2014/0276810 A1 | 9/2014 | Raybin et al. |
| 2015/0105789 A1 | 4/2015 | Raybin et al. |

FOREIGN PATENT DOCUMENTS

WO   WO 99/16365   4/1999

* cited by examiner

*Primary Examiner* — Wade Miles
(74) *Attorney, Agent, or Firm* — Bookoff McAndrews, PLLC

(57) ABSTRACT

A snare may a loop at a distal end of the elongate member and defining an inner area. The loop may have an inner surface facing and exposed in the inner area, wherein a first section of the inner surface has an edge sharper than a second section of the inner surface.

16 Claims, 4 Drawing Sheets

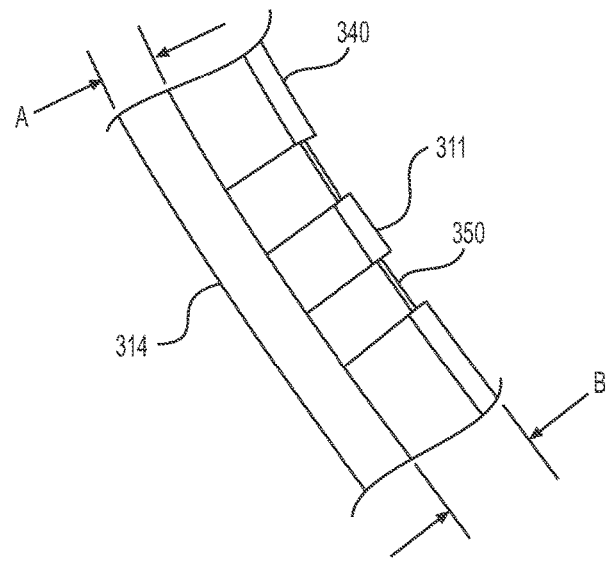
FIG. 4
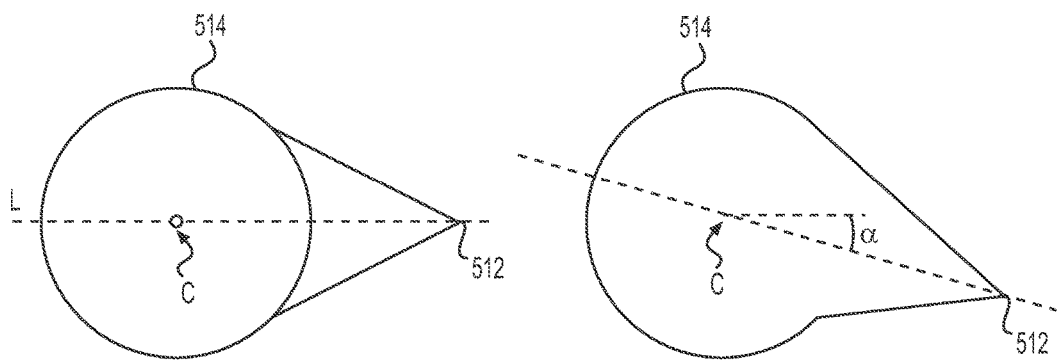
FIG. 5A  FIG. 5B

SNARE DESIGN FOR IMPROVED TRACTION

CROSS-REFERENCE TO RELATED APPLICATIONS

This application claims the benefit of U.S. Provisional Application No. 62/120,155, filed Feb. 24, 2015, the entirety of which is incorporated herein by reference.

TECHNICAL FIELD

Embodiments of the present disclosure relate generally to medical devices for grasping or cutting tissue. In particular, embodiments of the present disclosure relate to snare devices.

BACKGROUND

A wide variety of medical techniques and instruments have been developed for diagnosis and/or treatment within a patient's body, such as within a patient's Gastrointestinal (GI) tract. Endoscopic Mucosal Resection (EMR), Endoscopic Sub-mucosal Resection (ESR), Polypectomy, Mucosectomy, etc., are minimally invasive treatment methods for both malignant and non-malignant lesions. Endoscopic medical procedures, such as, for example, EMR, may be used to excise sessile adenomas or other unwanted tissue (i.e., tumors attached to a bodily surface) from the surface of an anatomical lumen. Such procedures often require the resection of one tissue plane while leaving an underlying tissue plane intact. Commonly, snares, designed as loops, have been used during such medical procedures, for resecting tissue from a target site. However, the conventional snares have a tendency to slip off the targeted tissue, and often require repeated efforts to capture the tissue before the resection procedure(s) can be successfully performed. Slippage may increase the length and cost of the procedure and decrease the efficiency.

Conventionally, a downward force on the snare is applied in an effort to improve traction between the snare and the unwanted or target tissue. This downward force is usually limited due to a lack of stiffness in the snare loop, however, causing the distal end of the snare loop to deflect away from the targeted tissue, thereby leading to improper placement of the snare. To control the deflection, the downward force may continue to be applied or it may be increased until the tissue is snared. Continued or increased applied force increases the possibility of accidentally damaging surrounding tissues (in particular underlying tissue layers, such as, e.g., the muscularis), as well as increasing the time and effort required to complete a procedure. Furthermore, it may sometimes be difficult to apply the necessary downward forces due to geometric and physical limitations.

SUMMARY

Embodiments of the present disclosure relate to, among other things, snare devices. Each of the embodiments disclosed herein may include one or more of the features described in connection with any of the other disclosed embodiments.

In one example, a snare may include an elongate member and a loop at a distal end of the elongate member and defining an inner area. The loop has an inner surface facing and exposed to the inner area, wherein a first section of the inner surface may have an edge extending radially about the loop and sharper than a second section of the inner surface, wherein the first portion may include a distally-facing portion of the inner surface.

Examples of the snare may additionally and/or alternatively include one or more other features. For example, the edge of the first section of the inner surface may be a single continuous, non-serrated sharp edge. In another example, the edge of the first section of the inner surface may be a serrated edge. The first section may be approximately 50 percent of the inner surface. The first section may be proximal of the second section. The edge may include serrated and non-serrated sharp portions. The first section of the inner surface may have a single sharp edge, and the second section may be curved without any sharp edges. A line from a center of a cross-section of the first section to the edge may be one of above or below a plane of the loop. The line may be up to 25 degrees from the plane. The line may be approximately 20 degrees below the plane. The edge of the first section may be arc-shaped to extend along an inner circumference of the loop. The loop may include only two legs opposite each other, and the edge may be on only one of the two legs, the other of the two legs may not have a sharp edge extending radially about the loop. Only the first section of the one of the two legs may have a sharp edge along the inner surface. The edge may have serrate and non-serrated portions. The edge may be on only distally-facing portions of the inner surface.

In another example, the snare may include an elongate member and a loop at a distal end of the elongate member and defining an inner area. The loop may have an inner surface facing and exposed to the inner area, wherein a first section of the inner surface may have an edge extending radially about the loop and sharper than a second section of the inner surface, wherein a line from a center of a cross-section of the first section to the edge may be one of above or below a plane of the loop.

Examples of the snare may additionally and/or alternatively include one or more other features. For example, the line may be up to 25 degrees from plane. The line may be below the plane. The line may be approximately 20 degrees below the plane. The edge of the first section may be arc-shaped to extend along an inner circumference of the loop. The first section may be proximal to the second section and at least a portion of the first section may be distally-facing.

In one example, a method for grasping tissue may include inserting a snare into a body and grasping tissue with the snare, wherein the snare may include an elongate member. The snare may further include a loop at a distal end of the elongate member and defining an inner area, wherein the loop may have an inner surface facing and exposed to the inner area, a first section of the inner surface may have an edge extending radially about the loop and sharper than a second section of the inner surface, and the first portion may include a distally-facing portion of the inner surface.

Examples of the method for grasping tissue may additionally and/or alternatively include one or more other features. For example, the first section may be proximal to the second section. The edge of the first section of the inner surface may be a single continuous, non-serrated sharp edge. The edge of the first section of the inner surface may be a serrated edge. The first section may be approximately 50 percent of the inner surface. The edge may include serrated and non-serrated sharp portions.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description serve to explain the principles of the disclosure.

FIG. 4 is an example of a section of a snare; and

FIGS. 5A-B are cross-sectional shapes of a snare, according to the present disclosure.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a patient. The term "proximal" refers to the end closest to the user when placing the device into the patient. When used herein, the term "approximately" may indicate a range of values within +/−5% of a stated value.

Overview

The present disclosure is drawn to various embodiments of snares. A snare, sometimes generally referred to as a snare loop, may be located at a distal end of a snare device. In some embodiments, a snare loop may be designed to improve traction on tissue and/or decrease slippage of the snare. The snare may include a sharp inner surface.

Exemplary Embodiments

Figure 1:
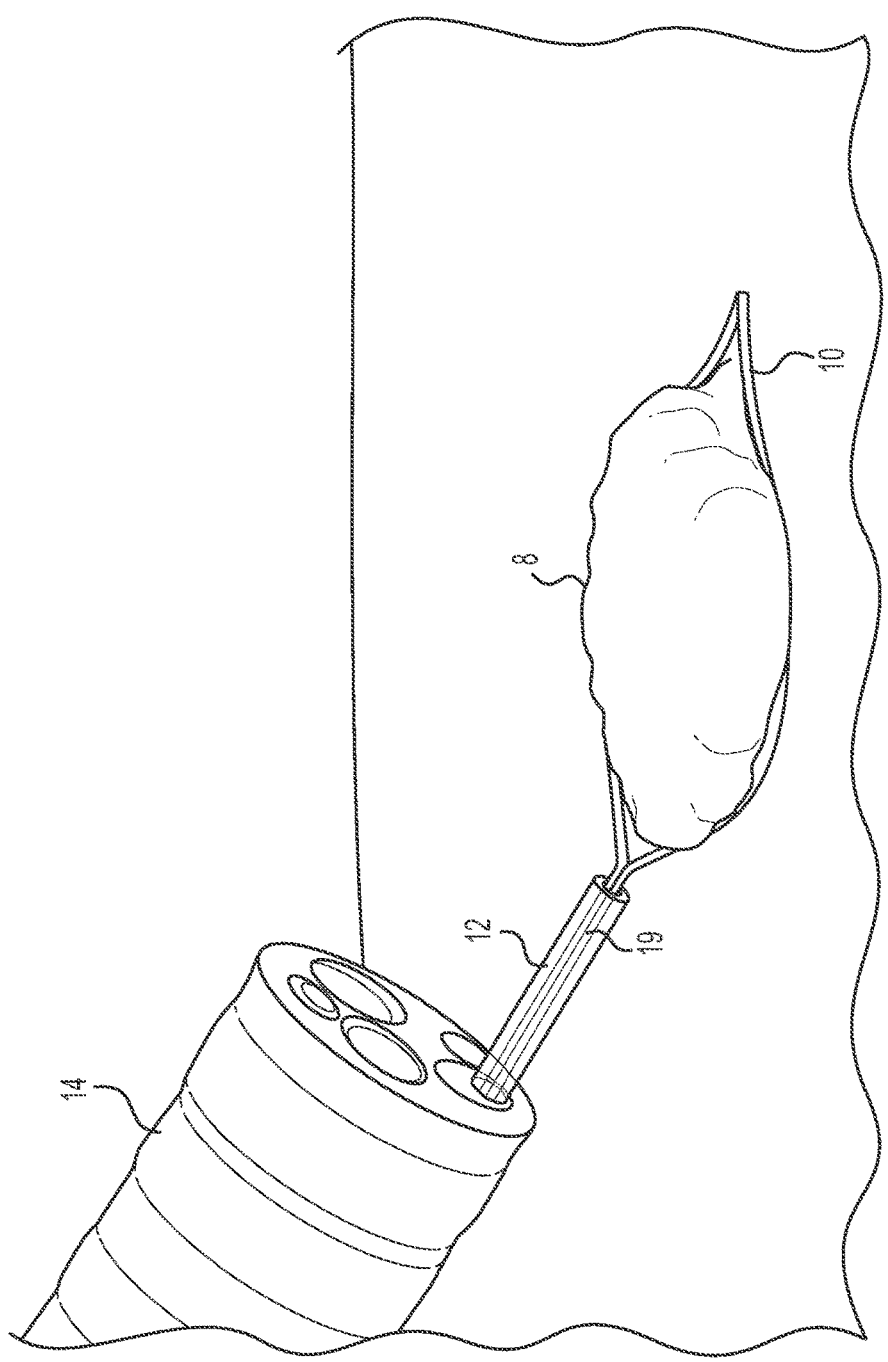
FIG. 1 illustrates an example of a snare within a patient's body.

FIG. 1 is an example of a snare 10 within a patient's body. Endoscopic device 14 (for example, an endoscope, colonoscope, or other device) may be inserted into an internal cavity of a patient, e.g., into the colon, the esophagus, or other portion of the GI tract, and may be used to locate tissue of interest, including abnormal tissue growths, such as polyp 8, in the internal cavity. A proximal end of snare 10 may be connected to, or integral with, an elongate member 19. The elongate member 19 may extend through a tube 12 in a lumen of endoscopic device 14. Upon locating polyp 8 or other tissue which is to be removed, the elongate member 19 may be pushed in the distal direction so that snare 10 is ejected from the distal end of tube 12 and endoscopic device 14. The snare 10 and the endoscopic device 14 may be manipulated from outside of the patient to pass the loop over the polyp 8 or other growth or tissue. The elongate member 19 may then be drawn in the proximal direction to tighten snare loop 10 around a base region or neck of the tissue or polyp 8, as shown in FIG. 1. It is often during this tightening step that snare 10 may slip off of polyp 8. Traditional snares may have smooth or rounded inner surfaces in contact with polyp 8. In the present disclosure, however, at least sections of the inner surface of snare 10 may be sharp (as further described with respect to FIGS. 2, 3A-C, 4, and 5A-B). The endoscopic assembly and configuration of FIG. 1 are merely exemplary, as the snares of this disclosure may be used in any device, in any configuration, and for any purpose.

Figure 2:
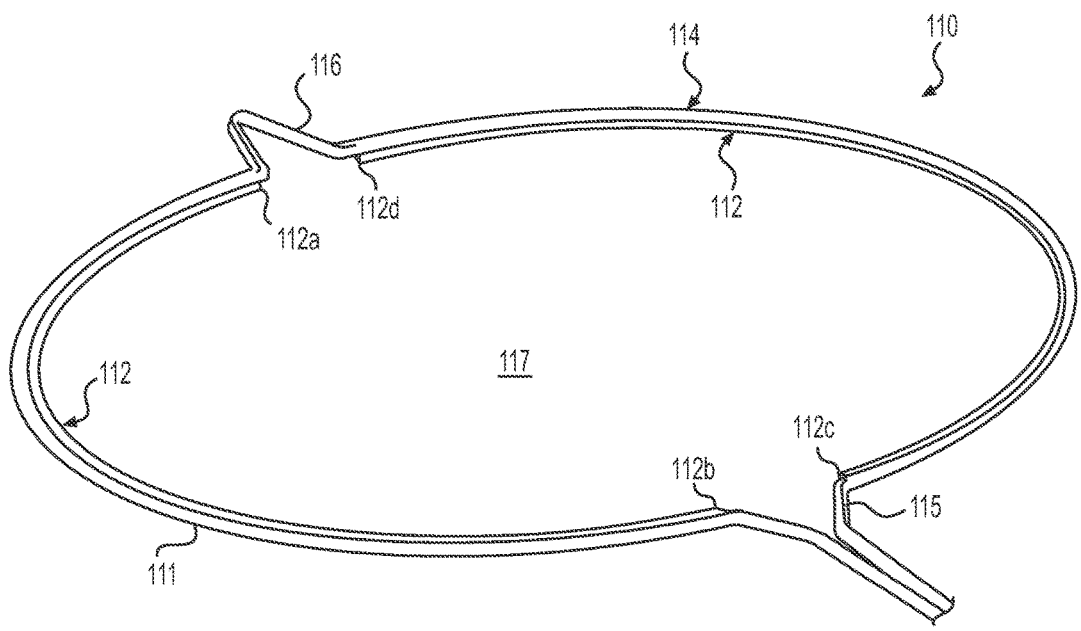
FIG. 2 illustrates an example of a snare with improved traction.

An exemplary snare 110 of the present disclosure may be substantially circular in shape when expanded, as shown in FIG. 2. The snare 110 may generally include a main body portion 111 connecting a proximal portion 115 and a distal portion 116. Main body 111, proximal portion 115, and distal portion 116 define an inner area 117. The proximal portion 115 may define a proximalmost boundary of the inner area 117, and the distal portion 116 may define a distalmost boundary of the inner area 117. Each of the proximal portion 115 and the distal portion 116 may be V-shaped, as shown in FIG. 2. The main body portion 111 of the snare 110 may include two sides or elongated "legs" connecting the proximal and distal portions 115, 116. In some examples, a snare of the present disclosure may not include proximal portion 115 and/or distal portion 116, but instead, the elongated legs may connected directly to each other, forming a single continuous loop. In one embodiment, the snare 110 may include a loop that can surround a portion of target tissue (e.g., polyp 8 of FIG. 1). The loop may be continuous, or the loop may have a small (e.g., less than approximately 25 percent of the loop) discontinuity or break, for example, near the proximal portion 115 of the snare 110. The snare 110 may be any other shape or configuration, however, including a polygonal loop, non-symmetrical loop, ellipsoid, or a basket. In other embodiments, the snare 110 may include multiple loops. The snare 110 may be a hot snare (capable of conducting electrocautery current) or a cold snare. The cross-sectional shape of snare 110 may be similar to the shapes shown in FIGS. 4 (a plan/top view of a leg) and 5A-B (taken perpendicular to the plane of the snare), which will be described in greater detail below. The snare 110 may be configured to collapse to facilitate passage into an endoscope (e.g., endoscopic device 14 of FIG. 1) or other device used to insert the snare 110 into a patient's body. Snare 110 may be formed from stainless steel, nitinol, or other biocompatible material.

As shown in FIG. 2, the snare 110 may include an outer surface 114 and may be shaped to define inner area 117. The outer surface 114 of the snare 110 may face away from the inner area 117. Outer surface 114 may be rounded without any sharp edges.

The snare 110 may have an inner surface opposite the outer surface 114 and facing and exposed to the inner area 117. Section 112 of the inner surface may have a sharp edge that extends radially about the snare 110 and about a point within inner area 117. A sharp edge may increase traction and decrease slippage, thereby increasing the ability to grasp and/or anchor tissue. For example, section 112 of the inner surface may dig into the target tissue (e.g. polyp 8 of FIG. 1) as the operator is tightening the loop, without necessarily cutting the tissue. This may ensure that traction is maintained and the target tissue is correctly captured.

Additionally or alternatively, in some implementations, a sharp edge may have the ability to cut through tissue, if the edge is applied with sufficient force. A sharp edge (e.g., like that of section 112 of the inner surface) may result in a cleaner cut. By creating a smaller radius at the tissue contact site, the snare 110 may more easily slide through the tissue, increasing the probability of polyp removal during the first attempt.

The inner surface along the entire inner circumference (or substantially the entire inner circumference) of the snare may include a sharp edge. Alternatively, as shown in FIG. 2, only certain sections of the inner surface may include a sharp edge. Sharp-edged sections 112 of the inner surface may reside on both sides (legs) of the main body 111 of the snare 110 but not within proximal portion 115 and distal portion 116. On one leg, a section 112 extends continuously from point 112b adjacent proximal portion 115 to point 112a adjacent distal portion 116. Similarly, on the opposite leg, a section 112 extends continuously from point 112c adjacent proximal portion 115 to point 112d adjacent distal portion 116, in a mirror image about the longitudinal axis of the snare. Sharp-edged sections 112 of the inner surface may have any shape. For example, sharp-edged sections 112 of inner surface may have a serrated edge, as will be further described with respect to FIG. 4. Sections 112 of the inner surface may have a continuous sharp edge, as will be further described with respect to FIGS. 5A-B.

Figure 3A:
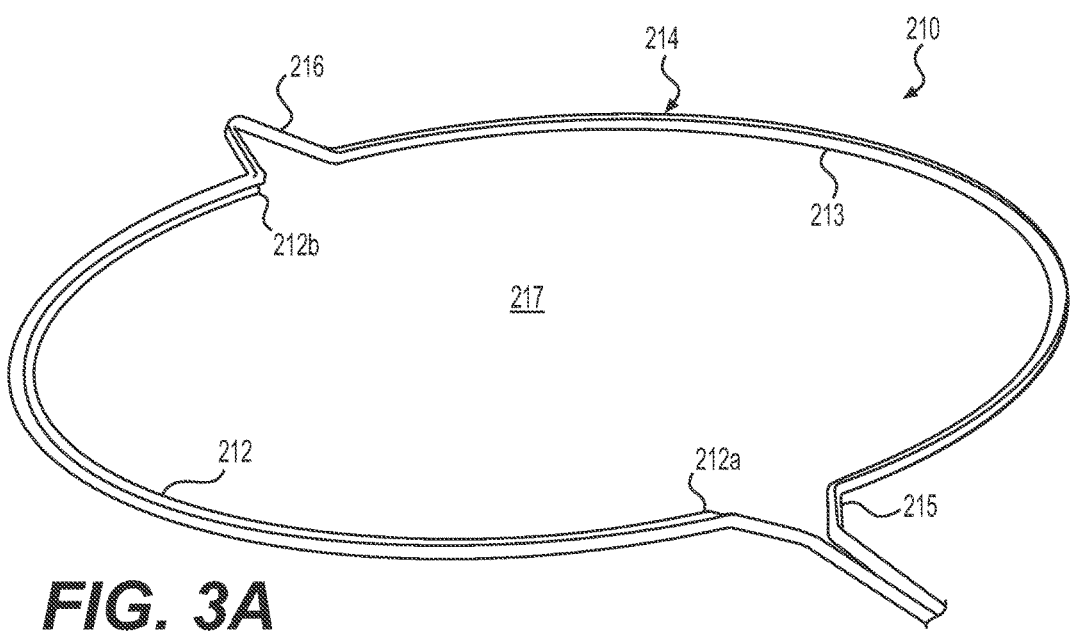
FIGS. 3A-3C illustrate examples of snares with improved traction, wherein the elements that may improve traction are implemented on certain sections of an inner surface of the snare.
Figure 3B:
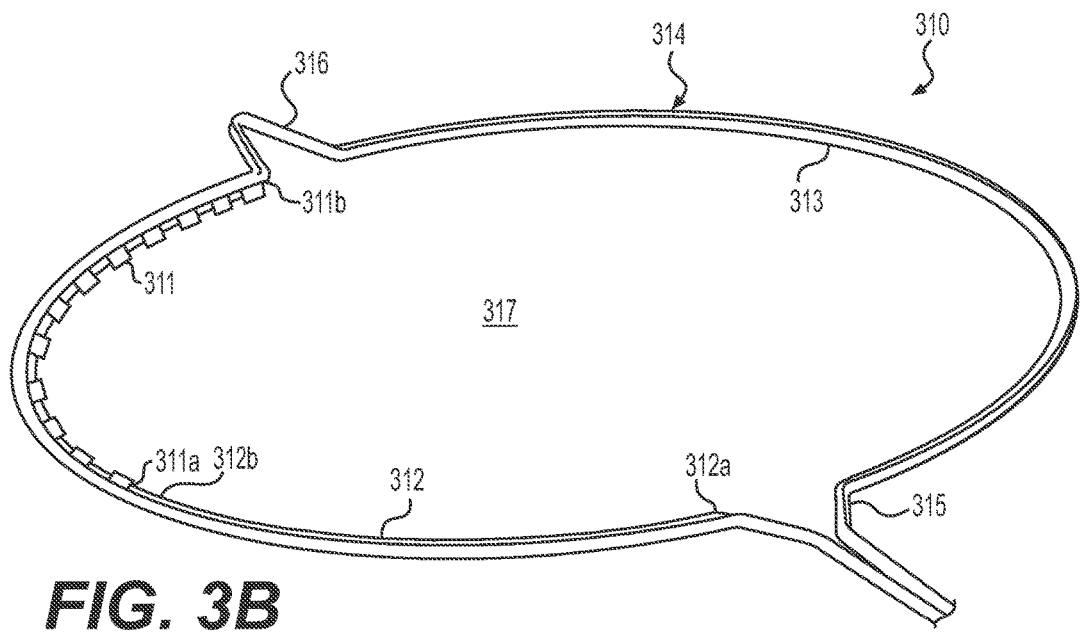
Figure 3C:
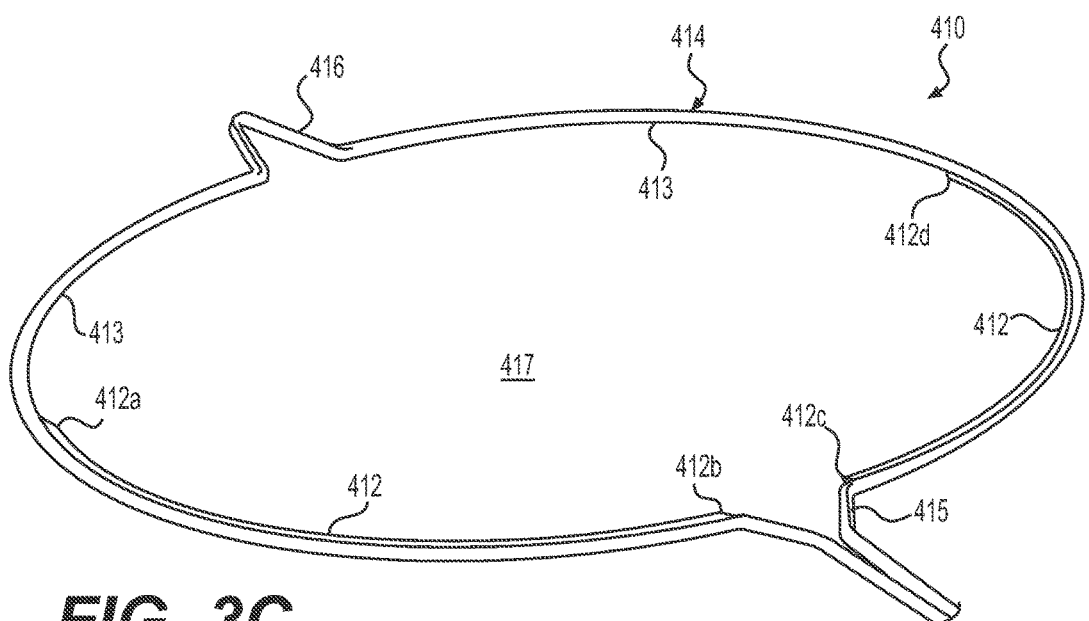

FIGS. 3A-C illustrate similar snares to snare 10 of FIG. 1 and/or snare 110 of FIG. 2. FIGS. 3A-C illustrate snares 210, 310, and 410, respectfully. Snares 210, 310, and 410 include an outer surface 214, 314, and 414 and define an inner area 217, 317, and 417. Outer surfaces 214, 314, and 414 may be rounded without any sharp edges.

FIGS. 3A-C illustrate additional examples in which only certain sections of the inner surface of the snare may be sharp. By not making some sections of the snare sharp, the necessary additional traction may be achieved while minimizing unintended trauma. For example, the more surface area of the tissue contacted by a sharp edge or surface, the greater the risk the tissue may be unintentionally cut. Regardless of the location of the sharp-edged sections, decreasing the amount of the inner surface of the snare that is sharp may reduce this risk. For example, in FIG. 3A, section 212 of the inner surface of snare 210 includes a sharp edge, while section 213 of the inner surface of snare 210 may be rounded without any sharp edges or points. That is, one leg of the snare has a sharp-edged section while the other leg of the snare does not. Section 212 may extend along the circumference of the inner surface between points 212a and 212b, as in FIG. 2. The section between points 212a and 212b is part of a first leg of snare 210. In some examples, section 213 is part of a second leg of snare 210. The first and second legs of snare 210 connect a proximal portion 215 and a distal portion 216. By only including a sharp edge or surface on a section of the circumference of snare 210, the risk of unintended trauma may be decreased, while still decreasing the occurrence of slippage.

In another example, as illustrated in FIG. 3B, both a serrated-edged inner surface (e.g., FIG. 4) and a continuous sharp edge may be disposed on a single snare. Snare 310 may include section 313 that may be rounded without any sharp edges or points, section 311 with a serrated-edged inner surface, and a section 312 with a continuous sharp edge. A section of snare without any sharp edges or points may be any section of the inner surface of snare 310. In the example shown in FIG. 3B, section 313 has no sharp edges or points and extends along the circumference of the inner surface of a first leg of snare 310. The first leg and a second leg of snare 310 may connect a proximal portion 315 and a distal portion 316. Sections 311 and 312 are disposed on the second leg. Section 312 extends along the circumference of the inner surface between 312a and 312b. A sharp-edged section may extend along any portion of the leg it may be disposed on. For example, section 312 may be disposed on approximately 5 percent to approximately 95 percent of a leg of snare 310. As shown in FIG. 3B, section 312 is disposed on approximately 50 percent of a leg of snare 310. Section 312 is disposed on distally-facing sections of the inner surface of the second leg. In some examples, section 311 may abut section 312. In other examples, a section similar to section 313, rounded without any sharp edges or points, may extend along the circumference of the inner surface between section 311 and 312. Section 311 extends along the circumference of the inner surface between points 311a and 311b. A serrated-edged section may extend along any portion of a leg. For example, such a section may be disposed on approximately 5 percent to approximately 95 percent of a leg of snare 310. As shown in FIG. 3B, serrated-edged section 311 is disposed on approximately 50 percent of a leg of snare 310. Section 311 is disposed on proximally-facing sections of the inner surface of a leg. In some embodiments, sections 311 and 312 may be disposed on different legs of the same snare.

The specific location of sections that are sharp versus sections that are not sharp may maximize traction while decreasing trauma. For example, as shown in FIG. 3C, sections 412 of the inner surface include sharp edges and are proximal to sections 413 of the inner surface of snare 410, which are rounded without any sharp edges or points. Sections 412 may have a serrated inner surface and/or a continuous sharp edge. Sections 412 are disposed on one or both legs and extend along the circumference of distally-facing surfaces of the inner surface. Sections 412 extend between points 412a and 412b on a first leg and between points 412c and 412d on a second leg. Points 412b and 412c are adjacent proximal portion 415, and points 412a and 412d are on a distally-facing inner surface of the snare. The first and second legs of snare 410 connect proximal portion 415 and distal portion 416 of FIG. 3C. Sharp-edged sections may extend along any portion of a leg. For example, such a section may be approximately 5 percent to approximately 95 percent of one or both legs of snare 410. As shown in FIG. 3C, sections 412 are disposed on approximately 50 percent of each leg of snare 410. Non-sharp sections may be any section of the inner surface of snare 410. In the example shown in FIG. 3C, section 413 (e.g., a section that may be rounded without any sharp edges or points) extends along the circumference of only proximally-facing surfaces of the inner surface. Sections 413 may be all of the inner surface that is distal to sections 412 and/or all sections that are not included in section 412. As another example, snare 410 may only have a single section 412 disposed on only one of the legs.

Configuring a snare so that a distally-facing section of the inner surface has a sharp-edge and a proximally-facing section does not (e.g., sections 412 and sections 413 of FIG. 3C), may decrease unintentional trauma, because, as explained with respect to FIG. 1, an operator may tighten a loop by pulling proximally on an elongate member connected to the snare loop. Pulling in the proximal direction may pull the section of the inner surface of snare 414 that is distal to the tissue toward the tissue. If the inner surface of snare 414 that is distal to the tissue is sharp, there may be a risk of cutting the tissue during the tightening process. Since, in the example illustrated in FIG. 3C, the only sections of the inner surface that are sharp (sections 412) are proximal to the tissue, this risk may be decreased, while these sharp sections 412 may still provide the necessary traction to prevent slipping.

The present disclosure is not limited to the examples illustrated in FIGS. 2 and 3A-C, but may include any combination of inner surfaces having sharp edges and non-sharp edges.

FIG. 4 illustrates an exemplary segment of any of the sharp-edged sections of the inner surfaces of FIGS. 2 and 3A-C. In one example, FIG. 4 illustrates the serrated section 311 of FIG. 3B. The perspective of FIG. 4 is such that portions facing the right side of the page are facing the inner area (e.g., 117 of FIG. 2, 217 of FIG. 3A, 317 of FIG. 3B, and/or 417 of FIG. 3C), and portions facing the left side of the page are facing away from the inner area (e.g., 117 of FIG. 2, 217 of FIG. 3A, 317 of FIG. 3B, and/or 417 of FIG. 3C). Sections 340 include a dull, flat, or rounded surface facing the inner area. The depth "B" of sections 340 (e.g., the distance they protrude into the inner area) may be between approximately one quarter and approximately twice the diameter of the portion labeled "A." Grooves 350 have a sharp edge and may not protrude as far into the inner area as sections 340. The configuration illustrated in FIG. 4 may decrease the occurrence of slippage as portions of the target tissue may sink into grooves 350. This sunk-in tissue may help to anchor the snare. In addition, a serrated edge may prevent premature tissue trauma by reducing the overall length of the sharp edges of the inner surface of the snare.

FIGS. 5A-B illustrate various examples of snare cross-sectional shapes for sections with sharp-edged inner surfaces. The sections of the snares of FIGS. 1, 2, and 3A-C with sharp inner surfaces (e.g., 112, 212, 311, 312, and/or 412) may have any of the shown cross-sectional shapes, in addition to any other cross-sectional shape that results in a sharp inner edge or surface. Both FIGS. 5A and 5B illustrate continuous sharp edges (e.g., section 312 of FIG. 3B), edges that extend about the circumference without any discontinuity within the sharp-edge section of a leg. The perspective of FIGS. 5A-B is such that portions facing the right side of the page are facing the inner area (e.g., 117 of FIG. 2, 217 of FIG. 3A, 317 of FIG. 3B, and/or 417 of FIG. 3C), and portions facing the left side of the page are facing away from the inner area (e.g., 117 of FIG. 2, 217 of FIG. 3A, 317 of FIG. 3B, and/or 417 of FIG. 3C).

FIG. 5A illustrates a continuous sharp edge 512 wherein a straight line L from the center C of leg 514 to the edge 512 extends into the inner area of the snare into the plane of the snare loop. FIG. 5A is merely exemplary. Alternatively, the continuous sharp edge 512 may be at any angle as compared to the plane of the snare loop. For example, as shown in FIG. 5B, the continuous sharp edge 512 may extend into the inner portion of a snare at a downward angle α, i.e., a straight line L from the center C of leg 514 to the edge 512 extends below the plane of the snare loop. Angling the edge downward, into the tissue, may help grab and lift the tissue. The angle of the continuous edge (or, more accurately, line L relative to the snare loop plane) may be between an approximately 25 degrees upward angle (above the plane) and an approximately 25 degrees downward angle (below the plane), preferably between an approximately 15 degree downward angle and an approximately 25 degrees downward angle or approximately 20 degrees downward.

The snares described herein may be used to remove portions of tissue from a patient. For example, embodiments of the disclosed snares may facilitate removal of unwanted tissue, such as cancerous polyps or lesions, from within a patient's body, including tissue disposed, for example, on the mucosal walls of the colon, esophagus, stomach, or duodenum. A physician also may desire to resect tissue in order to conduct a biopsy or other examination. At least one benefit of the disclosed is that increased traction on the tissue may improve tissue contact with the snare, which in turn may improve the transmission of the electricity used to aid in cutting the tissue (e.g., with hot snares).

The snares described herein may be formed by any method that allows at least a section of the inner surface to include a sharp edge. For example, a die assembly may be used to create a sharp-edged inner surface. A snare wire may be pressed between two forming plates to create the desired geometry. A snare wire of the present disclosure may also be formed by extrusion. For example, a snare wire may be formed by extruding monofilament stainless steel wire through an extrusion die that shapes the inner face to match the appropriate angle and geometry. In some implementations, to further improve the gripping strength of the wire, the wire may be chemically/plasma etched. This process removes the outer layers of the chemical bonds from the surface by blasting the unmasked/exposed portions with free radicals increasing the surface energy and thus increasing its grip on the tissue.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A snare, comprising:
a member; and
a loop at a distal end of the member and defining an inner area;
the loop having an inner surface facing and exposed to the inner area, wherein a first section of the inner surface has a plurality of first edges extending radially about the loop and that are sharper than a second section of the inner surface, the first section also including a plurality of atraumatic second edges, wherein the plurality of first edges and the plurality of second edges alternate circumferentially with one another in the first section, wherein the loop includes only two legs opposite each other, and the first section is on only one of the two legs, the other of the two legs not having a sharp edge extending radially about the loop.

2. The snare of claim 1, wherein the first section is approximately 50 percent of the inner surface.

3. The snare of claim 1, wherein each of the first edges and second edges of the first section is arc-shaped to extend along an inner circumference of the loop.

4. A snare, comprising:
a member; and
a loop at a distal end of the member and defining an inner area;
the loop having an inner surface facing and exposed to the inner area, wherein a first section of the inner surface has a plurality of first edges extending radially about the loop and that are sharper than a second section of the inner surface, wherein a line from a center of a cross-section of the first section to a given first edge is one of above or below a plane of the loop, wherein the first section also includes a plurality second edges each extending further radially inward than each of the plurality of first edges, wherein each of the plurality of second edges is atraumatic, wherein the loop includes only two legs opposite each other, and the first section is on only one of the two legs, the other of the two legs being entirely atraumatic.

5. The snare of claim 4, wherein the line is up to 25 degrees from the plane.

6. The snare of claim 5, wherein the line is below the plane.

7. The snare of claim 5, wherein the line is approximately 20 degrees below the plane.

8. The snare of claim 4, wherein the edge of the first section is arc-shaped to extend along an inner circumference of the loop.

9. A snare, comprising:
a member; and
a loop at a distal end of the member and defining an inner area, wherein a central longitudinal axis extends through the loop;
the loop having an inner surface facing and exposed to the inner area, wherein a first section of the inner surface has a plurality of first edges extending radially about the loop and that are sharper than a second section of the inner surface, wherein the first section also includes a plurality of second edges each extending further radially inward toward the central longitudinal axis than each of the plurality of first edges, wherein each of the plurality of second edges is atraumatic, wherein the loop includes only two legs opposite each other, the first section is on only a first leg of the two legs, and a second leg of the two legs not having a sharp edge extending radially about the loop and/or being entirely atraumatic.

10. The snare of claim 9, wherein the plurality of first edges and the plurality of second edges alternate circumferentially with one another in the first section.

11. The snare of claim 10, wherein
the plurality of first edges and the plurality of second edges are located on the first leg.

12. The snare of claim 11, wherein:
the first leg of the snare includes a continuous sharp edge facing the central longitudinal axis of the loop; and
the continuous sharp edge is proximal to the plurality of first edges and the plurality of second edges.

13. The snare of claim 9, wherein:
the loop includes an outer surface facing away from the central longitudinal axis; and
the outer surface is atraumatic.

14. The snare of claim 13, wherein the outer surface does not have any sharp edges.

15. The snare of claim 11, wherein:
distal ends of the first leg and the second leg are coupled to a bent distal portion of the loop; and
proximal ends of the first leg and the second leg are coupled to a bent proximal portion of the loop.

16. The snare of claim 12, wherein:
the loop includes an outer surface facing away from the central longitudinal axis;
the outer surface is atraumatic and without any sharp edges;
distal ends of the first leg and the second leg are coupled to a bent distal portion of the loop; and
proximal ends of the first leg and the second leg are coupled to a bent proximal portion of the loop.

\* \* \* \* \*